(12) United States Patent
Shimomura (10) Patent No.: US 7,613,487 B2
(45) Date of Patent: Nov. 3, 2009

(54) INSTRUMENT FOR NONINVASIVELY MEASURING BLOOD SUGAR LEVEL

(75) Inventor: Yoshiaki Shimomura, Omura (JP)

(73) Assignee: Nagasaki Prefectural Government (JP)

( * ) Notice: Subject to any disclaimer, the term of this patent is extended or adjusted under 35 U.S.C. 154(b) by 0 days.

(21) Appl. No.: 11/734,122

(22) Filed: Apr. 11, 2007

(65) Prior Publication Data

US 2007/0203405 A1    Aug. 30, 2007

Related U.S. Application Data

(63) Continuation of application No. PCT/JP2004/015676, filed on Oct. 15, 2004.

(51) Int. Cl.
*A61B 5/1455* (2006.01)
(52) U.S. Cl. ........................ 600/316; 600/322
(58) Field of Classification Search .............. 600/310, 600/316, 319, 322
See application file for complete search history.

(56) References Cited

U.S. PATENT DOCUMENTS

| | | | |
|---|---|---|---|
| 5,551,422 A * | 9/1996 | Simonsen et al. ........... | 600/322 |
| 5,910,109 A | 6/1999 | Peters et al. | |
| 6,192,261 B1 | 2/2001 | Gratton et al. | |
| 6,411,373 B1 * | 6/2002 | Garside et al. ............... | 356/39 |
| 6,990,364 B2 | 1/2006 | Ruchti et al. | |
| 2004/0068163 A1 | 4/2004 | Ruchti et al. | |

FOREIGN PATENT DOCUMENTS

| | | |
|---|---|---|
| DE | 19807939 C1 | 9/1999 |
| JP | 2-163634 | 6/1990 |
| JP | 2-191434 | 7/1990 |
| JP | 5-176917 | 7/1993 |
| JP | 9-182740 | 7/1997 |
| JP | 9-318529 | 12/1997 |
| JP | 2001-513351 | 9/2001 |
| KR | 1020040020878 A | 3/2004 |

OTHER PUBLICATIONS

Katsuhiko Maruko, et al., IEEE Journal of Selected Optics in Quantum Electronics, vol. 9, No. 2, pp. 322 to 330, 2003.
H.M. Heise et al., Artificial Organs, 18(6) pp. 439 to 447, 1994.
A. Ishimaru: Wave Propagation and Scattering in Random Media, Academic Press, New York, 1978.
Simulation of Optical-CT Imaging for a Highly Scattering Body ($2^{nd}$ Report, Fan-Beam Type), Journal of the Japan Society of Mechanical Engineers, vol. 59, 561 B, pp. 338 to 340, 1993. (with English translation of the paragraph referred in the present application).

* cited by examiner

*Primary Examiner*—Eric F Winakur
*Assistant Examiner*—Etsub D Berhanu
(74) *Attorney, Agent, or Firm*—St. Onge Steward Johnston & Reens LLC (57) ABSTRACT

A small and portable instrument for measuring blood sugar level of a human body noninvasively with no error comprising a light source control section for irradiating the measurement part of a finger with irradiation lights in two different near-infrared wavelength regions, photodetectors for receiving lights and of the irradiation lights quantities of transmitted lights. A relative transmittance, i.e. the ratio of the quantities of transmitted lights of the same wavelength detected at the two positions, is calculated for each wavelength and the blood sugar level is determined using the relative transmittance of each wavelength.

8 Claims, 9 Drawing Sheets

INSTRUMENT FOR NONINVASIVELY MEASURING BLOOD SUGAR LEVEL

CROSS-REFERENCE TO RELATED APPLICATIONS

The present application is a continuation of pending International patent application PCT/JP2004/015676 filed on Oct. 15, 2004 which designates the United States, the content of which is incorporated herein by reference.

FIELD OF THE INVENTION

The present invention relates to an instrument for noninvasively measuring the blood sugar level of a human body, and more particularly, to a technique for noninvasively measuring the blood sugar level of a human body without incurring an error by the use of transmitted light from the human body which can be obtained by irradiating the human body with a light of specific wavelength.

BACKGROUND OF THE INVENTION

In persons with diabetes, sugar is not accumulated in the muscles or the liver due to a deficiency of insulin secreted from the liver or an unresponsiveness of body cells to insulin. Therefore, glucose concentration in the blood, that is, blood sugar level is increased, thereby causing various complications such as retinopathy, neural disorder, nephropathy, and the like. Since the number of diabetes patients in Japan is 6.9 million and the number including patients with pre-diabetes group is more than 13 million, diabetes has become a serious national disease. In the present treatment for diabetes, a complete curing method has not been provided yet. For that reason, blood sugar level is maintained at an adequate level by an insulin injection or dietary treatment while measuring blood sugar levels.

At present, blood sugar level is measured by the use of a measuring instrument utilizing a glucose sensing method which electrochemically analyzes a glucose oxidase reaction for the taken blood to convert the analyzed value into the blood sugar level. A portable measuring instrument for measuring blood sugar level is used for daily management of the blood sugar level of a diabetes patient has already been commercialized. In such a blood sugar level test, there have been problems such as pain accompanied with blood drawing several times a day, infection caused by the needle, and the like. Accordingly, it has been required to have an instrument for measuring the blood sugar level noninvasively which does not require blood drawing and can measure a change in the blood sugar level in a day in real-time.

There has been disclosed a technique for irradiating the human body with light of a wavelength in a near-infrared region, measuring diffusely reflected light or transmitted light from the human body by using a spectroscope, and calculating the blood sugar level of the human body on the basis of the spectrum of the diffusely reflected light or the transmitted light (for example, refer to Non-Patent Documents 1 and 2 and Patent Document 1). Non-Patent Document 1 proposes a method of irradiating the light of a wavelength in the near-infrared region to the skin of the forearm and a standard reflecting plate by turns, measuring the spectrum of each diffusely reflected light by using the spectroscope and the like on the basis of the each diffusely reflected light, and measuring the blood sugar level by a multivariate analysis on the basis of a diffusion reflectance spectrum determined by the ratio of the spectrum of the diffusely reflected light of the skin of the forearm and the standard reflecting plate. Patent Document 1 proposes a method of irradiating the light of wavelength in the near-infrared region on a finger or the like, detecting the transmitted light thereof, evaluating absorbances for the specific wavelengths of 944 nm and 964 nm, and measuring the blood sugar level on the basis of the absorbance values.

However, according to the Non-Patent Document 1, a complicated spectroscope equipped with a diffraction grating and the like has been needed in order to irradiate the light of the wavelength in the near-infrared region on the skin of the forearm and measure the consecutive spectrum of the diffusely reflected light. That is, reflectance data of the light of a consecutive wavelength is needed so as to calculate the blood sugar level, and the above-mentioned spectroscope is needed to obtain the reflection spectrum after irradiating the human body with the light from a white light source having the light of wavelength in such a region. Since each diffusely reflected light from the standard reflecting plate and the human body is measured by turns, a change in light source causes a measurement error. In such a method of measuring the blood sugar level based on such white light source or the spectroscope, it was difficult to miniaturize and portablize the measuring instrument of the blood sugar level which can be carried easily for the diabetes patients to manage their daily blood sugar level.

Figure 9:
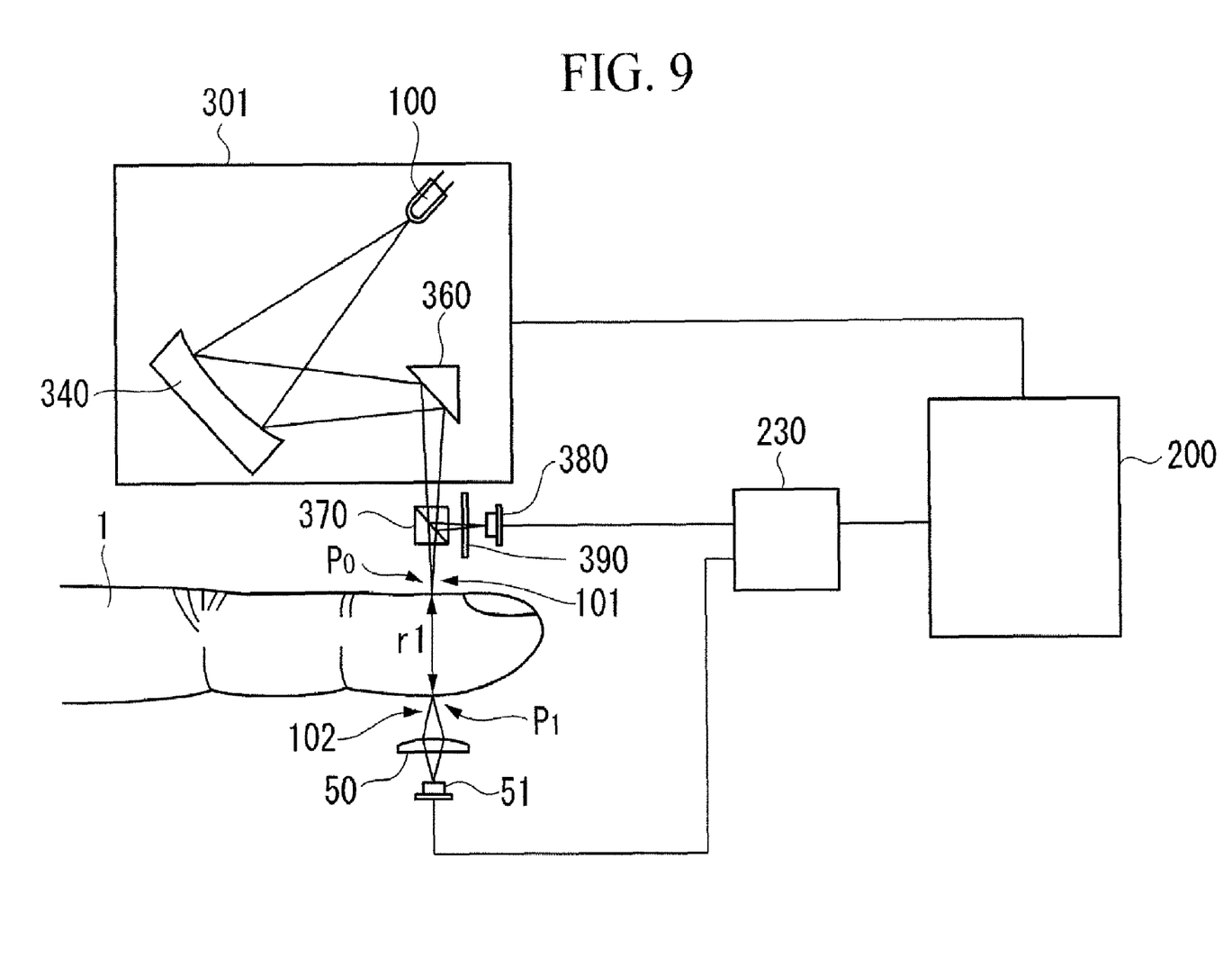
FIG. 9 is an explanatory view of an conventional instrument for noninvasively measuring blood sugar level.

On the other hand, in Patent Document 1, there has been proposed an instrument for measuring the blood sugar level by the use of light of the two specific wavelengths and the transmitted light thereof. This technique is described with reference to FIG. 9. The measuring instrument shown in FIG. 9 is equipped with a light source 100 generating near-infrared light, a diffraction grating 340, and a reflecting mirror 360 for irradiating a finger 1 only with the predetermined monochromatic light from the near-infrared light; and a sampling prism 370, an ND filter 390, and a photodetector 380 for detecting a part of the dispersed monochromatic light 101. In addition, the measuring instrument is equipped with a lens 50 and a photodetector 51 for detecting transmitted light 102 from the human finger 1; a signal processing section 230 which amplifies detection signals from the photodetectors 51 and 380 to digitize the signals; and a central control section 200. The central control section 200 calculates a transmittance T of the finger 1 on the basis of the detection signals from the photodetectors 51 and 380 amplified and digitized in the signal processing section 230 by the following formula.

$$T = I_1/I_0 \quad (1.1)$$

Wherein, $I_0$ is the irradiated light quantity of the irradiated light 101 and calculated by multiplying the detection signal detected by the photodetector 380 by a constant value. In addition, $I_1$ s light quantity of the transmitted light 102 and calculated by multiplying the detection signal detected by the photodetector 51 by a constant value. Here, the two wavelengths of 944 nm and 964 nm are selected as the wavelength of the irradiated light 101, and the transmittances for each wavelength are represented as $T_1$ and $T_2$. Then, the blood sugar level C is calculated by the following formula.

$$C = k_0 + k_1 * ABS_1/ABS_2 \quad (1.2)$$

Wherein, $ABS_1$ and $ABS_2$ can be obtained by the formulae: $ABS_1 = -\ln(T_1)$ and $ABS_2 = -\ln(T_2)$, respectively, $k_0$ and $k_1$ represent coefficients determined by a least squares method by the use of the actually measured blood sugar level. Here, the white light source is used as the light source. However, when semiconductor lasers of 944 nm and 964 nm are used as the two different wavelengths, there can be achieved the instrument for noninvasively measuring the blood sugar level which does not need a complicated spectroscope equipped with the diffraction grating and the like.

However, in this prior invention, a linear distance $r_1$ between an irradiated position $P_0$ of the irradiated light 101 and a detected position $P_1$ of the transmitted light 102 is slightly changed depending on the size of the finger 1. Due to the amount of such a slight change, there has been a problem that a significant measurement error occurs in the calculation of the blood sugar level C by the aforementioned formula. Further, even the irradiated position $P_0$ is disposed in the same side of the detected position $P_1$ at a distance of the linear distance $r_1$ so as not to be affected by the size of the finger, there is still a problem in that a significant measurement error occurs in the calculation of the blood sugar level C by the aforementioned formula (1.2) because the transmittance represented as the formula (1.1) changes due to the expansion or contraction of a blood vessel changing in response to the heart rate.

(Non-Patent Document 1)
Katsuhiko Maruko, et. al., IEEE Journal of Selected Optics in Quantum Electronics, Vol. 9, No. 2, pp. 322 to 330, 2003
(Non-Patent Document 2)
H. M. Heise et. al., Artificial Organs, 18(6) pp439 to 447, 1994
(Patent Document 1)
Japanese Unexamined Patent Application Publication No. 5-176917

SUMMARY OF THE INVENTION

An object of the present invention is to provide a small and portable instrument for noninvasively measuring a blood sugar level which can measure the blood sugar level of a human body noninvasively and accurately.

Configurations of the invention are as follows.

1) An instrument for noninvasively measuring blood sugar level including an irradiation device irradiating a measurement part of a human body with light of a plurality of different wavelengths; a transmitted light quantity detecting device receiving the transmitted light, which is the light from the irradiation device transmitted through the measurement part of the human body, at two positions spaced at different distances so as to detect the quantity of the transmitted light; and a calculation device calculating a relative transmittance, which is a ratio of the quantities of the transmitted light of the same wavelength at the two positions detected by the transmitted light quantity detecting device, for each wavelength so as to determine the blood sugar level of the human body by the use of the relative transmittance of each wavelength.

2) The instrument for noninvasively measuring the blood sugar level according to the above 1), wherein the irradiation device irradiates the light of two different wavelengths, and the calculation device calculates coefficients $k_0$ and $k_1$ in the formula by the use of the pre-measured blood sugar level and relative transmittances $R_{\lambda 1}$ and $R_{\lambda 2}$, and calculates the blood sugar level C in accordance with the following formula: $C=k_0+k_1*\ln(R_{\lambda 1})/\ln(R_{\lambda 2})$, in which, of the quantities of the transmitted light detected at the two positions, the quantity of the light transmitted through a shorter distance is represented as $I_{1,\lambda 1}$ and $I_{1,\lambda 2}$, and the quantity of the light transmitted through a longer distance is represented as $I_{2,\lambda 1}$ and $I_{2,\lambda 2}$, and the relative transmittances $R_{\lambda 1}$ and $R_{\lambda 2}$ of the two different wavelengths are represented by the following formulae: $R_{\lambda 1}=I_{2,\lambda 1}/I_{1,\lambda 1}$ and $R_{\lambda 2}=I_{2,\lambda 2}/I_{1,\lambda 2}$.

3) The instrument for noninvasively measuring the blood sugar level according to the above 1), wherein the irradiation device irradiates the light of two different wavelengths, and the calculation device calculates coefficients $k_0$ and $k_1$ in the formula by the use of the pre-measured blood sugar level and the absorbances $A_1$ and $A_2$, and calculates the blood sugar level C in accordance with the following formula: $C=k_0+k_1*A_1/A_2$, in which, of the quantities of the transmitted light detected at the two positions, the quantity of the light transmitted through a shorter distance is represented as $I_{1,\lambda 1}$ and $I_{1,\lambda 2}$, the quantity of the light transmitted through a longer distance is represented as $I_{2,\lambda 1}$ and $I_{2,\lambda 2}$, the relative transmittances $R_{\lambda 1}$ and $R_{\lambda 2}$ of the two different wavelengths are represented as the following formulae: $R_{\lambda 1}=I_{2,\lambda 1}/I_{1,\lambda 1}$ and $R_{\lambda 2}=I_{2,\lambda 2}/I_{1,\lambda 2}$, and the absorbances of the two different wavelengths $A_1$ and $A_2$ are represented by the following formulae on the basis of the relative transmittances $R_{\lambda 1}$ and $R_{\lambda 2}$: $A_1=-\ln(R_{\lambda 1})$ and $A_2=-\ln(R_{\lambda 2})$.

4) The instrument for noninvasively measuring the blood sugar level according to the above 1) or 2), in which the lights of two different wavelengths irradiated by the irradiation device are selected within the range of 900 to 1,100 nm.

5) The instrument for noninvasively measuring the blood sugar level according to the above 1), wherein the irradiation device irradiates light of three different wavelengths, and the calculation device calculates coefficients $k_0$ and $k_1$ in the formula by the use of the pre-measured blood sugar level and relative transmittances $R_{\lambda 1}$, $R_{\lambda 2}$, and $R_{\lambda 3}$, and calculates the blood sugar level C in accordance with the following formula: $C=k_0+k_1*\ln(R_{\lambda 1}/R_{\lambda 3})/\ln(R_{\lambda 2}/R_{\lambda 3})$, in which, of the quantities of the transmitted light detected at the two positions, the quantity of the light transmitted through a shorter distance is represented as $I_{1,\lambda 1}$, $I_{1,\lambda 2}$, and $I_{1,\lambda 3}$ and the quantity of the light transmitted through a longer distance is represented as $I_{2,\lambda 1}$, $I_{2,\lambda 2}$, $I_{2,\lambda 3}$, and the relative transmittances $R_{\lambda 1}$, $R_{\lambda 2}$, and $R_{\lambda 3}$ of the three wavelengths are represented by the following formulae: $R_{\lambda 1}=I_{2,\lambda 1}/I_{1,\lambda 1}$, $R_{\lambda 2}=I_{2,\lambda 2}/I_{1,\lambda 2}$, and $R_{\lambda 3}=I_{2,\lambda 3}/I_{1,\lambda 3}$.

6) The instrument for noninvasively measuring the blood sugar level according to the above 1), wherein the irradiation device irradiates light of three different wavelengths, and the calculation device calculates coefficients $k_0$ and $k_1$ in the formula by the use of the pre-measured blood sugar level and absorbances $A_1$, $A_2$, and $A_3$, and calculates the blood sugar level C in accordance with the following formula: $C=k_0+k_1*(A_1-A_3)/(A_2-A_3)$, in which, of the quantities of the transmitted light detected at the two positions, the quantity of the light transmitted through a shorter distance is represented as $I_{1,\lambda 1}$, $I_{1,\lambda 2}$, and $I_{1,\lambda 3}$ and the quantity of the light transmitted through a longer distance is represented as $I_{2,\lambda 1}$, $I_{2,\lambda 2}$, and $I_{2,\lambda 3}$, the relative transmittances $R_{\lambda 1}$, $R_{\lambda 2}$, and $R_{\lambda 3}$ of the three different wavelengths are represented by the following formulae: $R_{\lambda 1}=I_{2,\lambda 1}/I_{1,\lambda 1}$, $R_{\lambda 2}=I_{2,\lambda 2}/I_{1,\lambda 2}$, and $R_{\lambda 3}=I_{2,\lambda 3}/I_{1,\lambda 3}$, and the absorbances of the three different wavelengths $A_1$, $A_2$, and $A_3$ are represented by the following formulae on the basis of the relative transmittances $R_{\lambda 1}$, $R_{\lambda 2}$, and $R_{\lambda 3}$: $A_1=-\ln(R_{\lambda 1})$, $A_2=-\ln(R_{\lambda 2})$, and $A_3=-\ln(R_{\lambda 3})$.

7) The instrument for noninvasively measuring the blood sugar level according to the above 5) or 6), in which, among the lights of the three different wavelengths irradiated by the irradiation device, two of the lights are selected within the range of 900 to 1,100 nm and the other light is selected within the range of 900 to 930 nm or 1,000 to 1,030 nm.

Each reference numeral in the attached drawings has the following meanings.

| | |
|---|---|
| 1 | FINGER |
| 10, 20, 30 | LIGHT SOURCE |
| 11, 21, 31 | IRRADIATED LIGHT |
| 12, 13 | TRANSMITTED LIGHT |
| 22, 23 | TRANSMITTED LIGHT |
| 32, 33 | TRANSMITTED LIGHT |
| 41 | LENS |
| 50, 60 | LENS |
| 40 | PRISM |
| 51, 61 | PHOTODETECTOR |
| 100 | WHITE LIGHT SOURCE |
| 101 | IRRADIATED LIGHT |
| 102, 103 | TRANSMITTED LIGHT |
| 110 | POWER SUPPLY FOR WHITE LIGHT SOURCE |
| 120 | LENS |
| 200 | CENTRAL CONTROL SECTION |
| 210 | DISPLAY SECTION |
| 220 | LIGHT SOURCE CONTROL SECTION |
| 230 | SIGNAL PROCESSING SECTION |
| 300, 301 | SPECTROSCOPE |
| 310, 320 | LENS |
| 311, 321 | SHUTTER |
| 330 | PRISM |
| 340 | DIFFRACTION GRATING |
| 350 | MULTI-CHANNEL DETECTOR |
| 360 | MIRROR |
| 370 | SAMPLING PRISM |
| 380 | PHOTODETECTOR |
| 390 | ND FILTER |
| 410, 420, 430 | LENS |
| 700, 701, 702 | OPTICAL FIBER |
| 710, 720, 730 | OPTICAL FIBER |

DETAILED DESCRIPTION OF THE INVENTION

Hereinafter, the present invention will be described in detail with reference to drawings if necessary.

(An Irradiation Device)

As for the best irradiation device, an irradiation device which irradiates light of three different wavelengths to nearly the same irradiated position is preferred.

(Wavelength of Irradiated Light)

As for the best wavelength of irradiated light, it is preferable that, among the three different wavelengths, two of the wavelengths are selected within the range of 900 to 1,100 nm and the other wavelength is selected within the range of 900 to 930 nm or 1,000 to 1,030 nm.

(A Transmitted Light Quantity Detecting Device)

As for the best transmitted light quantity detecting device, the detecting device which detects transmitted light at two positions spaced at different distances from the irradiated position of the light from the irradiation device is preferred.

(A Calculation Device)

As for the best calculation device, it is preferable that, on the basis of the two detected transmitted lights, the relative transmittance, which is a ratio of the two transmitted lights, be calculated for every three different wavelengths, and a blood sugar level be calculated in accordance with a formula (1.8) on the basis of the three relative transmittances.

(A Transmitted Light)

As for the best transmitted light, the transmitted light detected by the transmitted light quantity detecting device at the same side as the irradiated position which is irradiated by the irradiation device on a human body is preferred.

According to the present invention, a plurality of light of different wavelengths is generated from a light source, and the light is irradiated onto a measurement part of the human body (for example, a finger, etc.) by the irradiation device. Irradiated light is scattered and absorbed inside of the human body and then emitted outside of the human body, whereby the light becomes transmitted light. The transmitted light is detected by a transmitted light quantity detecting device at two positions spaced at different distances from an irradiated position of the light. On the basis of the two detected transmitted lights, a relative transmittance, which is a ratio of the two transmitted lights, is calculated for each wavelength. On the basis of the relative transmittance, the blood sugar level of the human body is determined. In the detected transmitted light, there is included information on the blood sugar level of the human body. Accordingly, it is possible to measure the blood sugar level of the human body noninvasively.

By using a light source of two or three different wavelengths, it is possible to have an instrument which does not need a complicated spectroscope to detect the spectrum of the transmitted light or reflected light, unlike the conventional instrument for measuring the blood sugar level using a white light source. In addition, it is possible to have an instrument for noninvasively measuring the blood sugar level whose measurement error is less affected even when a linear distance between an irradiated position of monochromatic light and a detected position of transmitted light is varied depending on the size of a person's finger which is the measurement part. Moreover, it is possible to have an instrument for noninvasively measuring the blood sugar level whose measurement error is less affected even when the quantity of the transmitted light is varied due to the expansion or contraction of a blood vessel changing in response to the heart rate.

Regarding each symbol of the quantities of the transmitted light $I_{1,\lambda 1}$ and $I_{2,\lambda 1}$ and the relative transmittance $R_{\lambda 1}$ used in the present invention, the value of $I_1$ and $O_2$ represents the detected positions, and $\lambda_1$, $\lambda_2$, and $\lambda_3$ represent the wavelengths. Hereinafter, each embodiment of the present invention will be described in detail with reference to drawings.

EMBODIMENT 1

Figure 1:
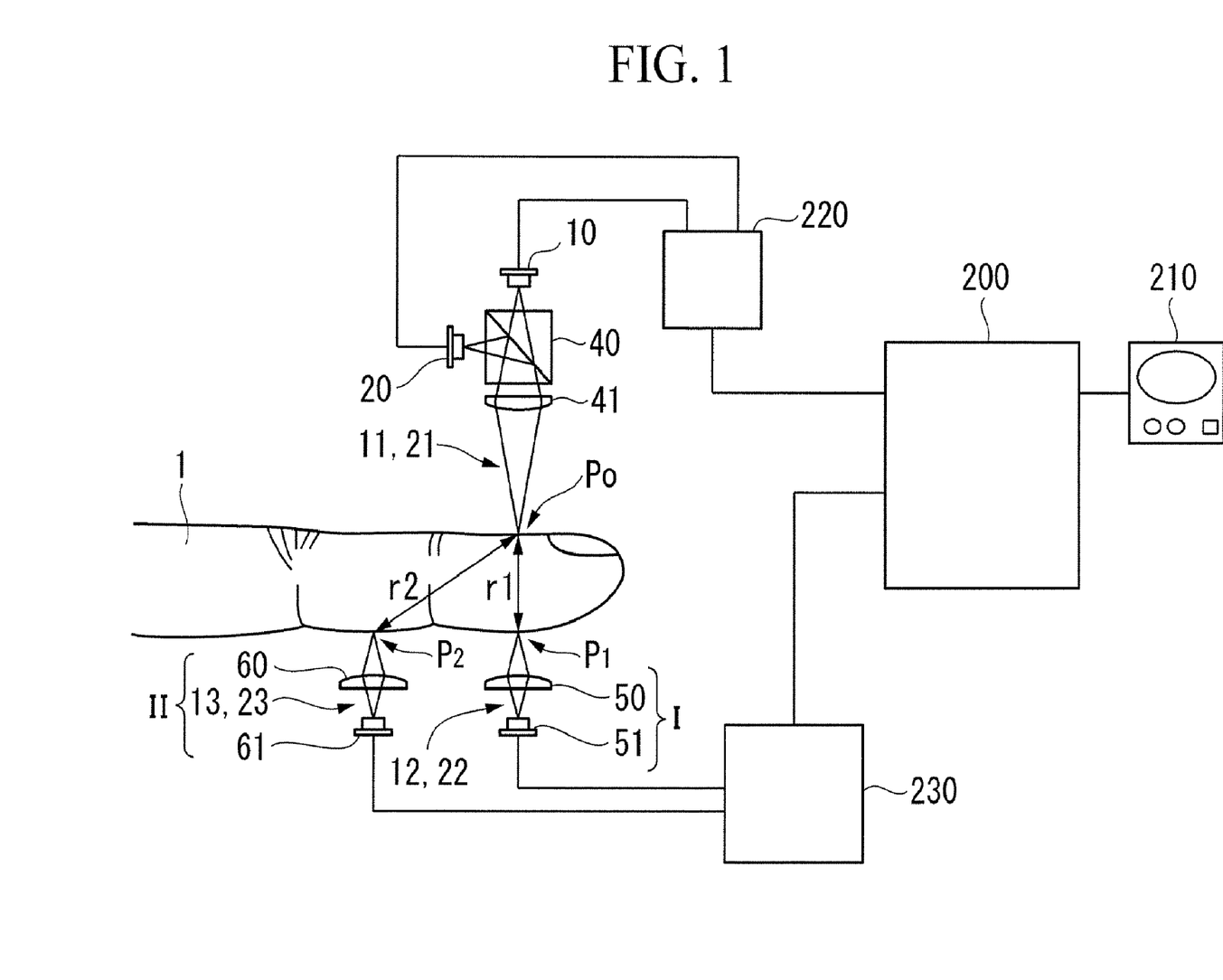
FIG. 1 is an explanatory view of an instrument for noninvasively measuring blood sugar level according to embodiment 1.

FIG. 1 is an explanatory view of an instrument for noninvasively measuring blood sugar level according to embodiment 1.

Figure 2:
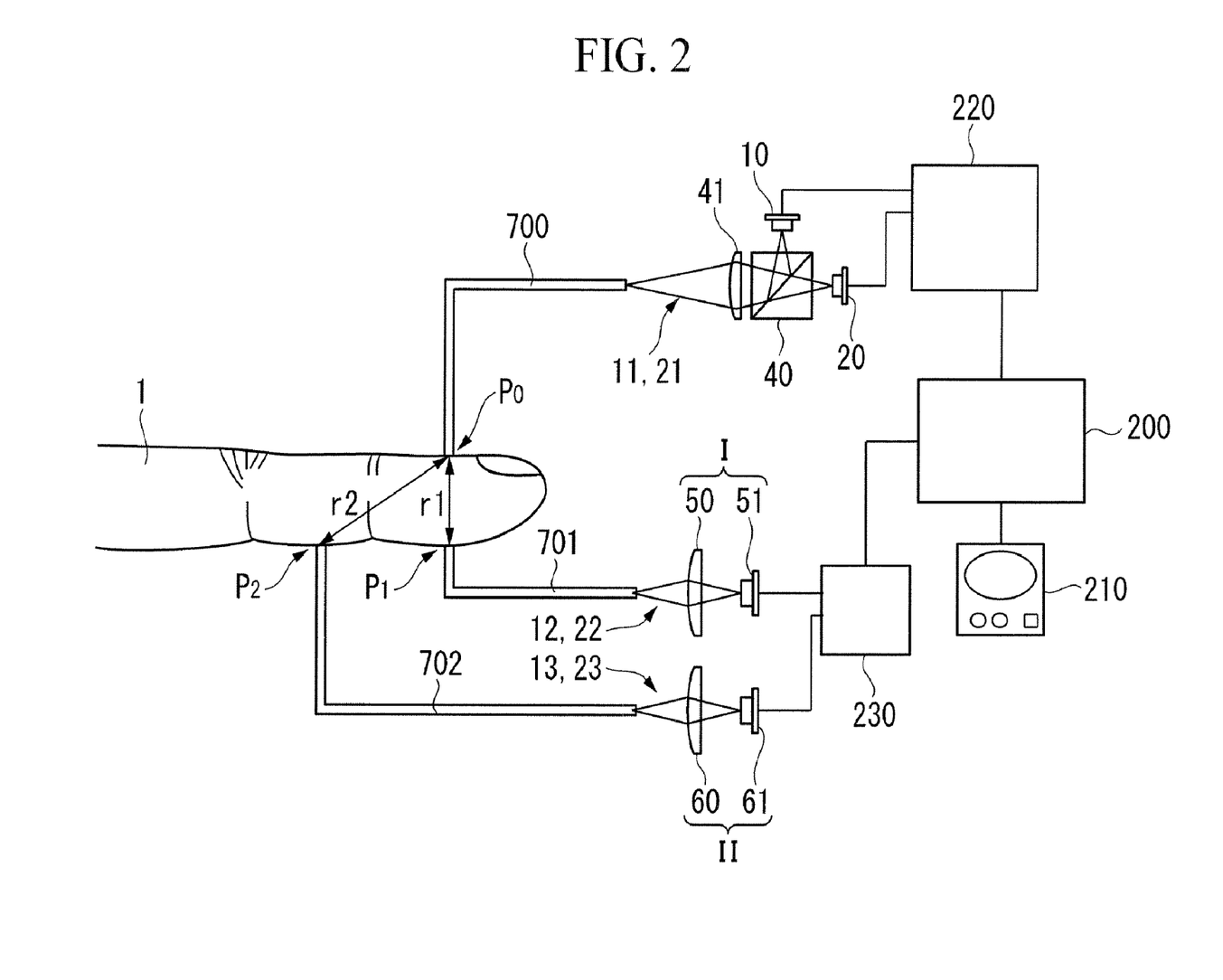
FIG. 2 is an explanatory view of an instrument for noninvasively measuring blood sugar level using an optical fiber according to another example of embodiment 1.

FIG. 2 is an explanatory view of an instrument for noninvasively measuring blood sugar level using an optical fiber according to another example of embodiment 1.

Figure 3:
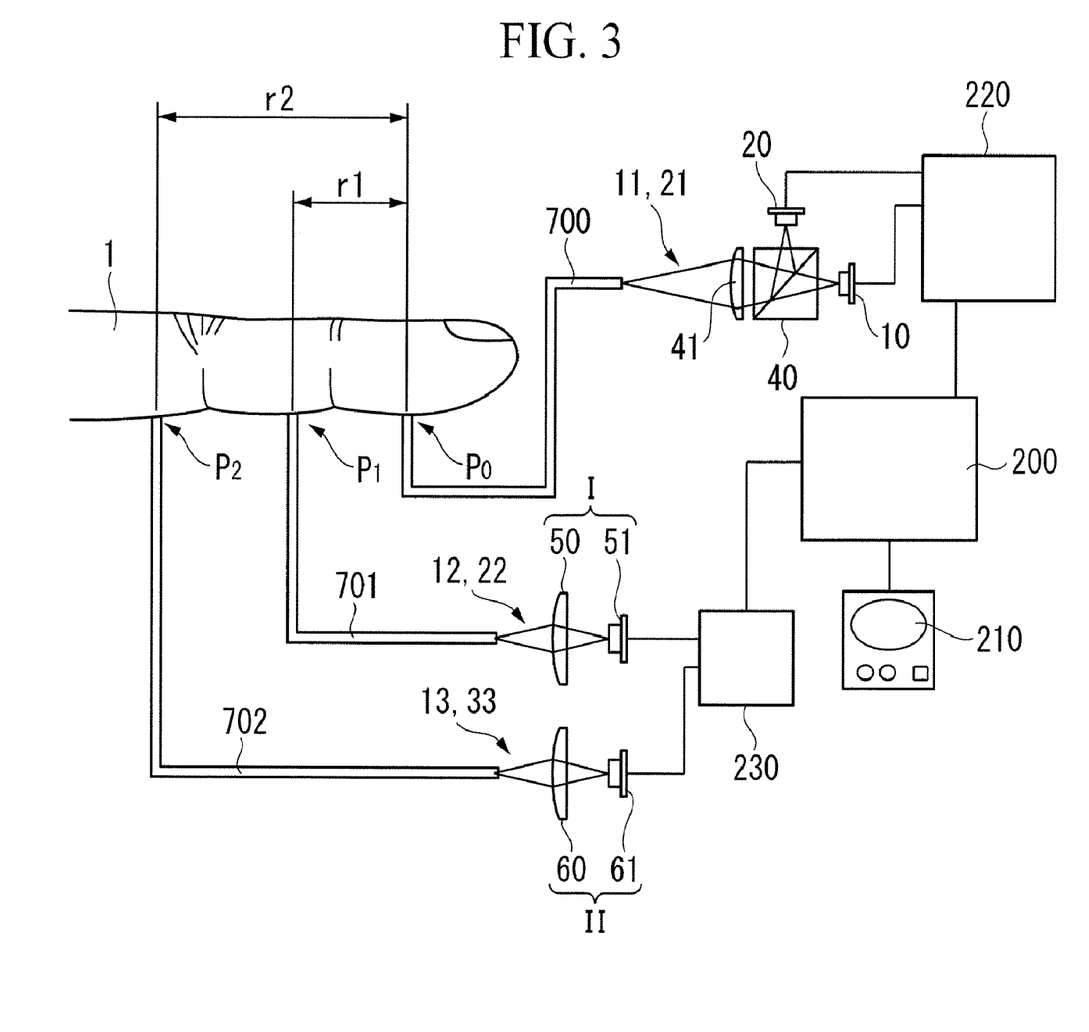
FIG. 3 is an explanatory view of an instrument for noninvasively measuring blood sugar level using an optical fiber according to another example of embodiment 1.

FIG. 3 is an explanatory view of an instrument for noninvasively measuring blood sugar level using an optical fiber according to another example of embodiment 1.

Reference numeral 1 is a finger; reference numerals 10, 20, and 30 are light sources; reference numerals 11, 21, and 31 are irradiated lights; reference numerals 12 and 13 are transmitted lights; reference numerals 22 and 23 are transmitted lights; reference numerals 32 and 33 are transmitted lights; reference numeral 41 is a lens; reference numerals 50 and 60 are lenses; reference numeral 40 is a prism; reference numerals 51 and 61 are photodetectors; reference numeral 100 is a white light source; reference numeral 101 is irradiated light; reference numerals 102 and 103 are transmitted lights; reference numeral 110 is a power supply for a white light source; reference numeral 120 is a lens; reference numeral 200 is a central control section; reference numeral 210 is a display section; reference numeral 220 is a light source control section; reference numeral 230 is a signal processing section; reference numerals 300 and 301 are spectroscopes; reference numerals 310 and 320 are lenses; reference numerals 311 and 321 are shutters; reference numeral 330 is a prism; reference numeral 340 is a diffraction grating; reference numeral 350 is a multi-channel detector; reference numeral 360 is a mirror; reference numeral 370 is a sampling prism; reference numeral 380 is a photodetector; reference numeral 390 is an ND filter; reference numerals 410, 420, and 430 are lenses; reference numerals 700, 701, and 702 are optical fibers; and reference numerals 710, 720, and 730 are optical fibers.

Embodiment 1 (refer to FIGS. 1 and 2): An instrument for measuring blood sugar level of embodiment 1 shown in FIG. 1 includes light sources 10 and 20 for irradiating irradiated lights 11 and 21 onto a finger 1, a reflective prism 40, and a lens 41. In addition, the instrument includes a transmitted light quantity detecting device 1 including a lens 50 and a photodetector 51 for detecting transmitted lights 12 and 22 which are transmitted from the finger 1; a transmitted light quantity detecting device II including a lens 60 and a photodetector 61 for detecting transmitted lights 13 and 23; a signal processing section 230; a central control section 200; a display section 210; and a light source control section 220.

In the central control section 200, blood sugar level of a human body is calculated in accordance with a calculation formula described later on the basis of a detection signal from the photodetectors 51 and 61 digitized in the signal processing section 230, and the blood sugar level is displayed on the display section 210. The light source control section 220 has a power supply section, which is not shown in the figures, to supply an electric current to the light sources 10 and 20. A direct current or a modulated current is supplied to the light source 10 (light source 20) in accordance with the instructions from the central control section 200.

An operation of the instrument for noninvasively measuring the blood sugar level having the above-mentioned configuration will be described.

The irradiated light 11 generated from the light source 10 is transmitted through the prism 40 and irradiated onto the finger 1 by the lens 41. The irradiated light 11 is scattered and absorbed inside of the finger 1 and then emitted outside of the finger 1 in every direction, whereby the light becomes transmitted light. After that, the transmitted light 12 from a position $P_1$ on the finger 1 spaced at a linear distance $r_1$ from an irradiated position $P_0$ of the irradiated light 11 is concentrated on a light receiving surface of the photodetector 51 by the lens 50. In addition, the transmitted light 13 from a position $P_2$ on the finger 1 spaced at a linear distance $r_2$ from the irradiated position $P_0$ of the irradiated light 11 is concentrated on a light receiving surface of the photodetector 61 by the lens 60. In FIG. 1, $r_2$ is longer than $r_1$, that is, $r_1 < r_2$, and a photodiode is used for the photodetectors 51 and 61.

From the photodetectors 51 and 61, detection signals in proportion to light intensities of the transmitted lights 12 and 13 are generated and the signals are digitized in the signal processing section 230. On the basis of the detection signals, a relative transmittance $R_{\lambda 1}$ is calculated in accordance with a calculation formula described later in the central control section 200 with the use of a computer.

Subsequently, a relative transmittance $R_{\lambda 2}$ of the irradiated light 21 is calculated as well as the calculating procedure of the relative transmittance $R_{\lambda 1}$ of the irradiated light 11 described above. When the calculating operation of a relative transmittance $R_{\lambda 2}$ of the irradiated light 21 is completed, the light sources 10 and 20 are turned off (lights-out) and an operation of measuring the blood sugar level of the finger 1 is completed. In the central control section 200, the blood sugar level of the finger 1 is calculated in accordance with the calculation formula described later on the basis of the calculated relative transmittance $R_{80\_1}$ and $R_{\lambda 2}$. The result is displayed on the display section 210.

Next, firmware that is a method of calculating the relative transmittances $R_{\lambda 1}$ and $R_{\lambda 2}$ performed in the central control section 200 will be described. The light quantity of the irradiated light 11 and the transmitted lights 12 and 13 for each wavelength are represented as $O_{0,\lambda 1}$, $I_{1,\lambda 1}$, and $I_{2,\lambda 1}$, respectively. The relative transmittance $R_{\lambda 1}$ of the finger 1 to the irradiated light 11 is represented by the following formula.

$$R_{\lambda 1} = I_{2,\lambda 1} / I_{1,\lambda 1} \tag{1.3}$$

When light quantity-voltage conversion coefficients of the photodetectors 51 and 61 are represented as $\beta_{51}$ and $\beta_{61}$ respectively, detection signals (voltage) $V_{51}$ and $V_{61}$ detected by the photodetectors 51 and 61 are represented by the following formulae.

$$V_{51} = \beta_{51} * I_{1,\lambda 1} \tag{1.4}$$

$$V_{61} = \beta_{61} * I_{2,\lambda 1} \tag{1.5}$$

On the basis of the each formula above, the relative transmittance $R_{\lambda 1}$ of the finger 1 is calculated by the following formula and is represented in a form independent of the light quantity $I_{0,\lambda 1}$ of the irradiated light 11.

$$R_{\lambda 1} = (\beta_{51}/\beta_{61}) * V_{61}/V_{51} \tag{1.6}$$

Here, the value in the round brackets ( ) is a unique constant of the instrument for measuring the blood sugar level and is simply corrected by the use of the light source of which light quantity has been known. In addition, the relative transmittance $R_{\lambda 2}$ of the finger 1 to the irradiated light 21 can be calculated in the same manner as a calculation of the relative transmittance $R_{\lambda 1}$ of the finger 1 to the irradiated light 11. The blood sugar level C of the finger 1 is calculated by the following formula by the use of the calculated relative transmittances $R_{\lambda 1}$ and $R_{\lambda 2}$.

$$C = k_0 + k_1 * \ln(R_{\lambda 1}) / \ln(R_{\lambda 2}) \tag{1.7}$$

Here, $k_0$ and $k_1$ represent coefficients determined by the least squares method by the use of the actually measured blood sugar level. Each of the two different wavelengths for measuring the blood sugar level is selected within the range of 900 to 1,100 nm in embodiment 1.

A laser can be used as the light sources 10 and 20 which generate the irradiated lights 11 and 21 within the aforementioned range. When a semiconductor laser is used as the laser, it is possible to have a small instrument for measuring the blood sugar level. Further, light emitting elements such as a light emitting diode and the like may be used for the light sources 10 and 20. When a white light source continuously generating light of a wavelength in a near-infrared region is used as the light sources 10 and 20, the small instrument for measuring the blood sugar level may be obtained by using an optical filter which transmits only the aforementioned wavelength from light sources 10 and 20. As shown in FIG. 2, the irradiated lights 11 and 21 from the light sources 10 and 20 may be irradiated onto the finger 1 by the use of the optical fiber 700, and the transmitted lights 12 and 13 (22 and 23) from detection spots $P_1$ and $P_2$ on the finger 1 may be light-guided to the transmitted light quantity detecting device I and II by the use of the optical fibers 701 and 702. Further, a measurement may be performed by disposing the optical fiber 700 shown in FIG. 2 on the detection side as shown in FIG. 3.

EMBODIMENT 2

Figure 4:
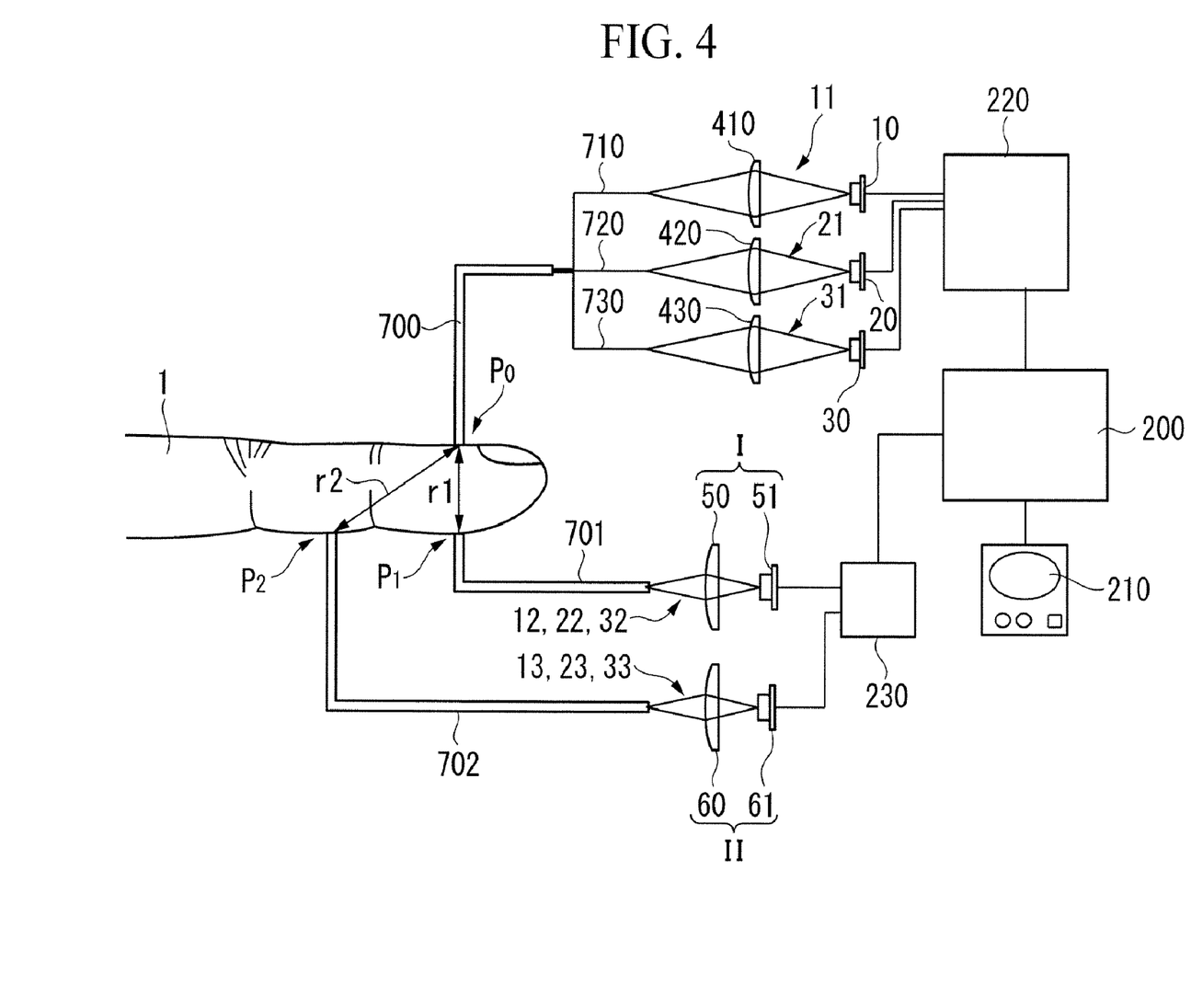
FIG. 4 is an explanatory view of an instrument for noninvasively measuring blood sugar level according to embodiment 2.

FIG. 4 is an explanatory view of an instrument for noninvasively measuring blood sugar level according to embodiment 2.

Figure 5:
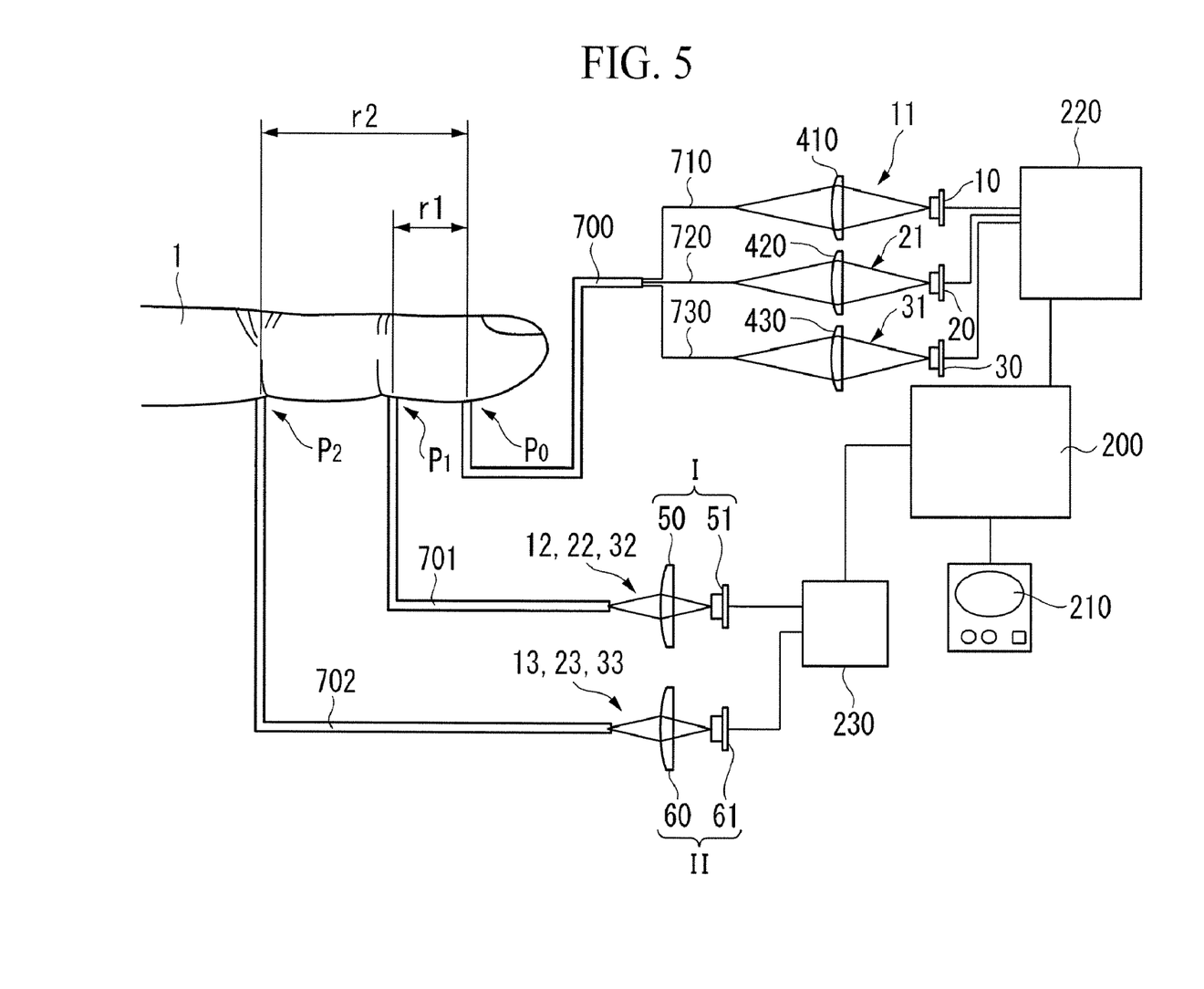
FIG. 5 is an explanatory view of an instrument for noninvasively measuring blood sugar level according to embodiment 2.

FIG. 5 is an explanatory view of an instrument for noninvasively measuring blood sugar level according to embodiment 2.

Embodiment 2 shown in FIG. 4 is an example of an instrument for noninvasively measuring blood sugar level by using three wavelengths. The instrument for measuring the blood sugar level according to embodiment 2 shown in FIG. 4 includes light sources 10, 20, and 30 for irradiating irradiated lights 11, 21, and 31 onto a finger 1; lenses 410, 420, and 430; optical fibers 710, 720, and 730; and an optical fiber 700 which bundles the optical fibers 710, 720, and 730 in a group to irradiate the irradiated lights 11, 21, and 31 onto the finger 1. In addition, the instrument includes a transmitted light quantity detecting device I including an optical fiber 701, a lens 50, and a photodetector 51 for detecting transmitted lights 12, 22, and 32 from the finger 1; a transmitted light quantity detecting device II including an optical fiber 702, a lens 60, and a photodetector 61 for detecting transmitted lights 13, 23, and 33; a signal processing section 230; a central control section 200; a display section 210; and a light source control section 220.

In the central control section 200, the blood sugar level of the human body is calculated in accordance with a calculation formula described later on the basis of detection signals from the photodetectors 51 and 61 digitized in the signal processing section 230, and the blood sugar level is displayed on the display section 210. The light source control section 220 has a power supply section, which is not shown in the figures, to supply an electric current to the light sources 10, 20, and 30. A direct current or a modulated current is supplied to the light source 10 (the light source 20 and the light source 30) in accordance with the instructions from the central control section 200. Relative transmittances $R_{\lambda,1}$, $R_{\lambda,2}$, and $R_{\lambda,3}$ of the finger 1 corresponding to the irradiated lights 11, 21, and 31 may be calculated in the same manner as in embodiment 1. The blood sugar level C of the finger 1 is calculated by the following formula by the use of the calculated relative transmittances $R_{\lambda,1}$, $R_{\lambda,2}$, and $R_{\lambda,3}$.

$$C = k_0 30\, k_1 * \ln(R_{\lambda,1}/R_{\lambda,3})/\ln(R_{\lambda,2}/R_{\lambda,3}) \quad (1.8)$$

Here, $k_0$ and $k_1$ represent coefficients determined by the least squares method by the use of the actually measured blood sugar level. As for the three different wavelengths for measuring the blood sugar level by using the formula (1.8), the wavelengths of the irradiated lights 11 and 21 are selected within the range of 900 to 1,100 nm, and the wavelength of the other irradiated light 31 is selected within the range of 900 to 930 nm or 1,000 to 1,030 nm in embodiment 2. The optical fiber 700 is disposed opposite the detection side of the finger 1 in FIG. 3, but may be disposed on the detection side as shown in FIG. 5.

EMBODIMENT 3

Figure 6:
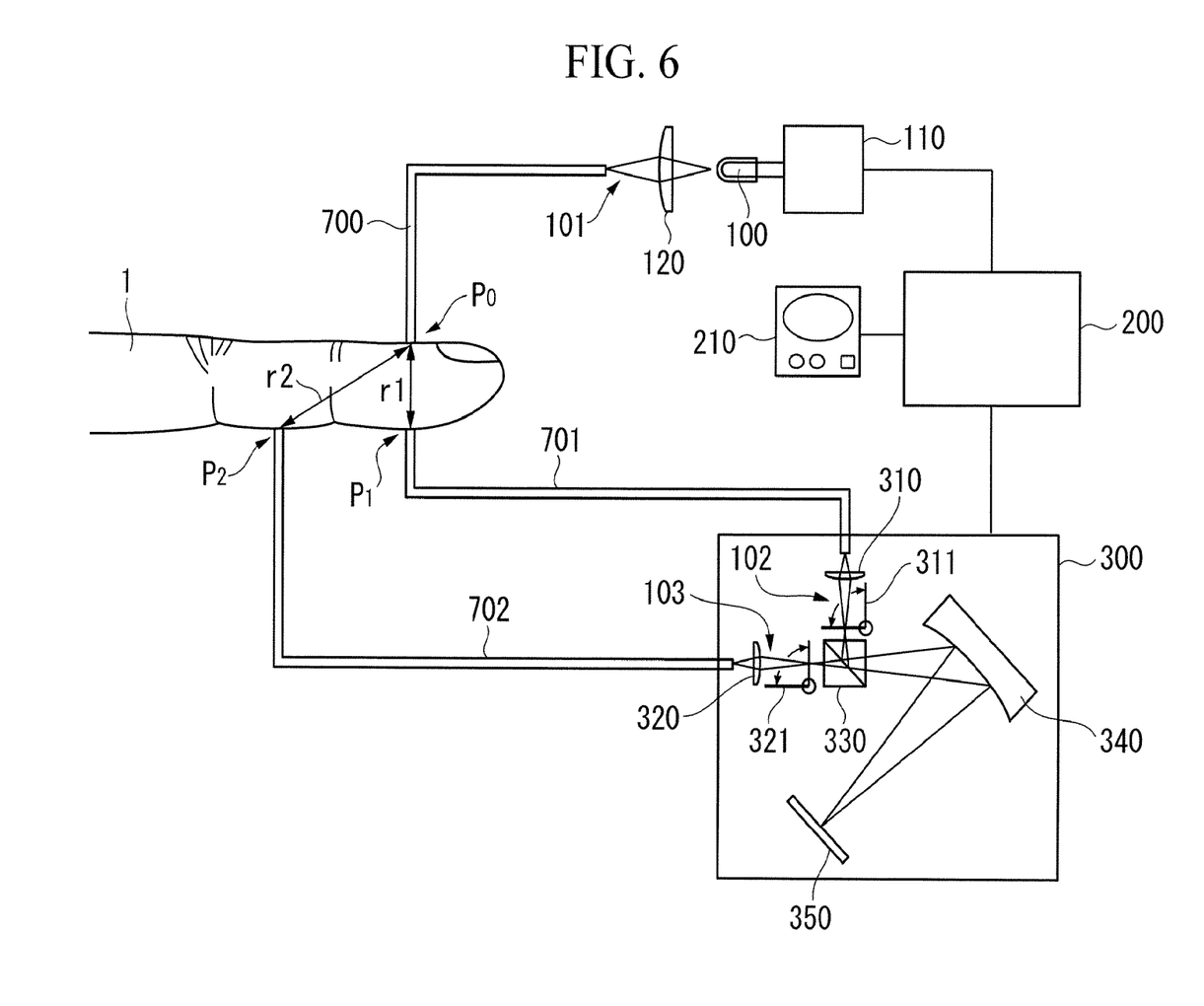
FIG. 6 is an explanatory view of an instrument for noninvasively measuring blood sugar level according to embodiment 3.

FIG. 6 is an explanatory view of an instrument for noninvasively measuring blood sugar level according to embodiment 3.

Figure 7:
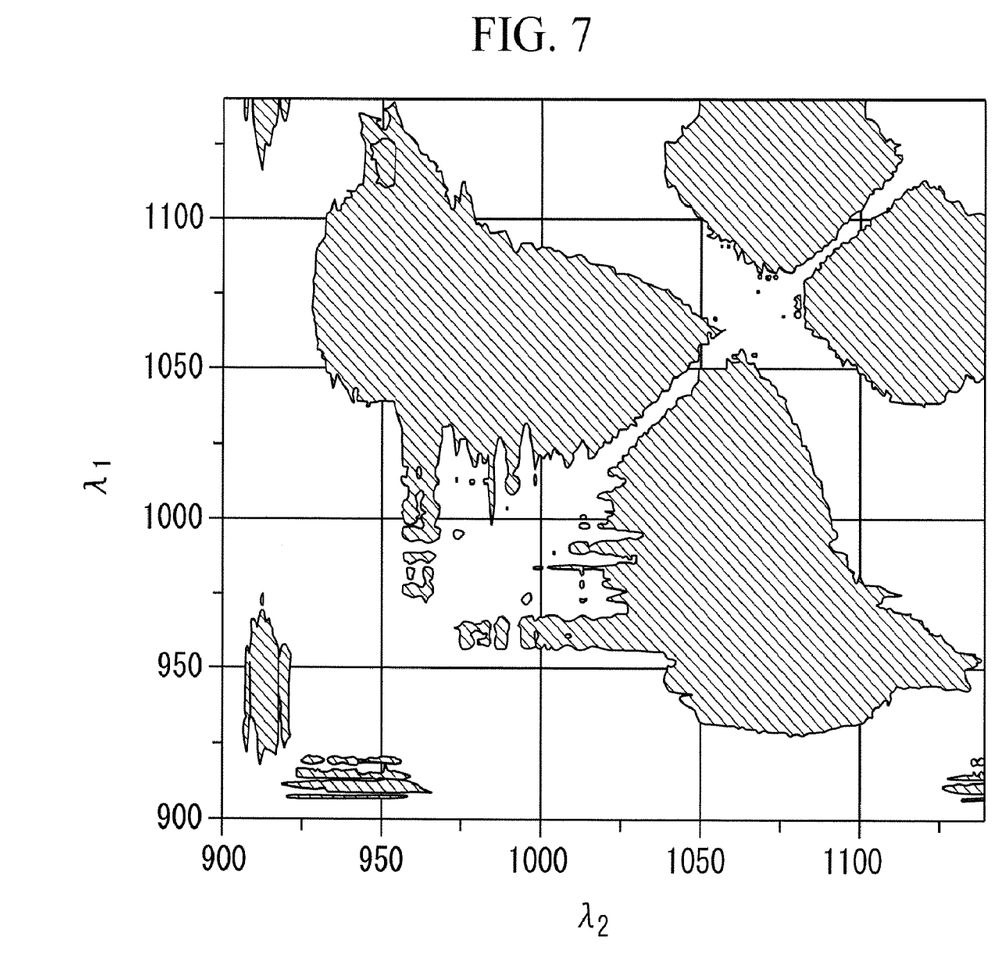
FIG. 7 is a drawing showing a combination region of an optimum wavelength in a scatterer selected as a model of a human body.

FIG. 7 is a drawing showing a combination region of the optimum wavelength in a scatterer selected as a model of a human body.

Figure 8:
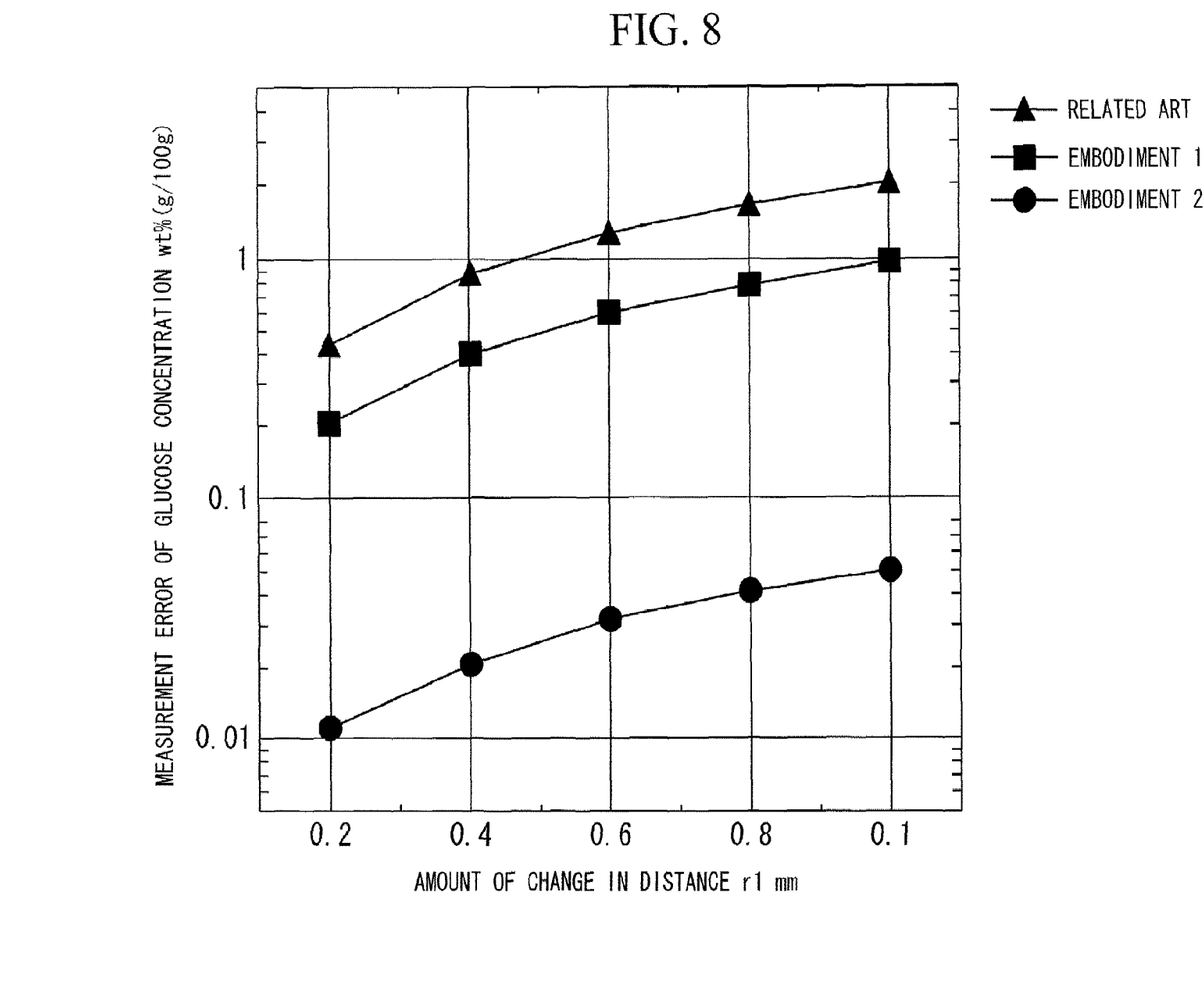
FIG. 8 is a drawing showing a relationship between the amount of change in detection distance $r_1$ and a measurement error of a blood sugar level.

FIG. 8 is a drawing showing a relationship between the amount of change in a detection distance $r_1$ and a measurement error of blood sugar level.

In embodiment 1 and 2, light irradiated onto a human body is described as limited to the two or three lights of different wavelengths. Accordingly, it is possible to have an instrument which does not need a complicated spectroscope for detecting the spectrum of the transmitted light or reflected light, unlike the conventional instrument for measuring the blood sugar level using a white light source. In addition, it is possible to have an instrument for noninvasively measuring the blood sugar level whose measurement error is less affected even when a linear distance between an irradiated position of irradiated light and a detected position of transmitted light is varied depending on the size of a measurement part such as a finger. Moreover, it is possible to have an instrument for noninvasively measuring the blood sugar level whose measurement error is less affected even when the quantity of the transmitted light is varied due to the expansion or contraction of a blood vessel changing in response to the heart rate.

On the other hand, even in an conventional instrument for noninvasively measuring a blood sugar level using the white light source and the spectroscope, it is possible to have an instrument whose measurement error is less affected even when a linear distance between an irradiated position of light and a detected position of the transmitted light is varied depending on the size of the measurement part such as the finger. In addition, it is possible to have an instrument whose measurement error is less affected even when the quantity of the transmitted light is varied due to the expansion or contraction of the blood vessel changing in response to the heart rate. Moreover, a standard reflecting plate described in Non-Patent Document 1 becomes unnecessary.

An example of the instrument for noninvasively measuring the blood sugar level applied to the conventional instrument using the white light source and the spectroscope will be described on the basis of the FIG. 6.

The instrument for noninvasively measuring the blood sugar level shown in FIG. 6 includes white light source 100 such as a halogen lamp having light of a wavelength in a near-infrared region and a power supply 110 thereof. Light 101 from the light source 100 is irradiated onto a finger 1 through a lens 120 and an optical fiber 700. The light 101 irradiated onto the finger 1 is scattered and absorbed inside of the finger 1 and then emitted outside of the finger 1 in every direction, whereby the light becomes transmitted light. The transmitted lights 102 and 103 of the light 101 from the optical fiber 700, which are from positions $P_1$ and $P_2$ on the finger 1 spaced at linear distances $r_1$ and $r_2$ from an irradiated position $P_0$ on the finger 1, are light-guided to a spectroscope 300 by the use of optical fibers 701 and 702.

The spectroscope 300 is equipped with lenses 310 and 320; shutters 311 and 321; a prism 330; a diffraction grating 340; and a multi-channel detector 350. A linear array sensor such as CCD is used for the multi-channel detector 350. In the case of measuring a transmission spectrum of the transmitted light 102 which is emitted from the position $P_1$, the shutter 311 is opened so that the transmission spectrum $S_1$ of the transmitted light 102 is obtained on the multi-channel detector 350. In this case, the shutter 321 is closed. In the same manner, in case of measuring a transmission spectrum $S_2$ of the transmitted light 103 which is emitted from the position $P_2$, the shutter 321 is opened so that the transmission spectrum $S_2$ of the transmitted light 103 is obtained on the multi-channel detector 350. In this case, the shutter 311 is closed. As mentioned above, a relative transmittance spectrum $T=S_2/S_1$ is calculated on the basis of the measured transmission spectra $S_1$ and $S_2$. On the basis of the obtained relative transmittance spectrum, an absorbance or a first differential value (or a second differential value) of absorbance is calculated, thereby the blood sugar level C can be determined using each formula above or a multivariate analysis described in Non-Patent Document 1.

The examination results according to a method of noninvasively measuring a blood sugar level of each embodiment are shown in FIGS. 7 and 8. For a scatterer selected as a model of a human body, a theoretical analysis is carried out about the correlation between an index $\gamma$ represented by the following formula (1.9) using a relative transmittance $R(\lambda_{i=1,2,3})$ and a glucose concentration in which the noninvasive measuring instrument shown in FIG. 5 is used, and a combination region of an wavelength having a square value of the correlation coefficient which satisfies the following formula: $R^2>0.995$ is shown as an oblique line in FIG. 7. The theoretical analysis was carried out with reference to the document 'A.Ishimaru: Wave Propagation and Scattering in Random Media, Academic Press, New York (1978)'. In this theoretical calculation, the linear distances $r_1$ and $r_2$ in FIG. 7 were set as 10 mm and 20 mm respectively. An equivalent scaterring coefficient is fixed regardless of the glucose concentration and a wavelength, and the general value of the human body 1.0 $mm^{-1}$ (reference: Journal of the Japan Society of Mechanical Engineers, Vol. 59, 561 B (1993), pp. 338 to 340) was used herein. In addition, for an absorption coefficient depending on the wavelength and the glucose concentration, a result actually measured by the use of a glucose solution was used. A wavelength $\lambda_3$ was set as 900 nm ($\lambda_3$=900 nm).

$$\gamma=\ln(R(\lambda_1)/R(\lambda_3))/\ln(R(\lambda_2)/R(\lambda_3)) \qquad (1.9)$$

In FIG. 7, it is determined that there is a combination of the optimum wavelengths $\lambda_1$ and $\lambda_2$ within the wavelength range of 900 to 1,100 nm in order to estimate the glucose concentration in accordance with the index $\gamma$. Next, in the instrument for measuring the blood sugar level according to embodiment 1 and 2, the result of analyzing a measurement error of the blood sugar level, in which the distances $r_1$ and $r_2$ in FIGS. 3 and 5 are varied, is shown in FIG. 8. The distance between the transmitted light detecting positions $P_1$ and $P_2$ was fixed as 10 mm. In the related art, it is assumed that an irradiated position $P_0$ is disposed on the same side as the detection position $P_1$. When the irradiated position is disposed on the same side as the detection position, effects caused by the size of the finger may be ignored but the quantity of the transmitted light is changed due to the expansion or contraction of a blood vessel changing in response to the heart rate. Such change in the quantity of the transmitted light may be considered to be caused seemingly by a variation of the distances $r_1$ and $r_2$. It is determined that the measurement error of the blood sugar level in embodiment 1 is reduced approximately to ½ as compared to the related art and the measurement error of the blood sugar level in embodiment 2 is reduced approximately to 1/40 as compared to the related art. That is, the expansion or contraction of the blood vessel changing in response to the heart rate as well as a variation of the thickness of the finger may change the quantity of the transmitted light, but the measurement error of the blood sugar level may be decreased as compared to the related art according to embodiment 1 and 2.

INDUSTRIAL APPLICABILITY

As described above, according to the present invention, light of a plurality of different wavelengths is irradiated onto a human body and the transmitted light thereof is detected at two positions spaced at different distances from an irradiated position of the light. In the detected transmitted light, information on the blood sugar level of the human body is included. Therefore, it is possible to measure the blood sugar level of the human body. In addition, it is possible to have an instrument which does not need a complicated spectroscope for detecting the spectrum of the transmitted light or reflected light, unlike the conventional instrument for measuring the blood sugar level using a white light source. Further, it is possible to have a small and lightweight instrument for measuring the blood sugar level because a small semiconductor laser or the like can be used as a light source. Furthermore, it is possible to have an instrument for noninvasively measuring the blood sugar level whose measurement error is less affected even when a quantity of the transmitted light changes depending on the variation of the size of a measurement part such as the finger or the expansion or contraction of the blood vessel.

The invention claimed is:

1. An instrument for noninvasively measuring a blood sugar level comprising:
   an irradiation device configured to irradiate a measurement part of a human body with the light of two different wavelengths;
   a transmitted light quantity detecting device configured to receive transmitted light, which is the light from the irradiation device transmitted through the measurement part of the human body, at two positions spaced at different distances so as to detect the quantity of the transmitted light; and
   a calculation device configured to calculate coefficients $k_0$ and $k_1$ by the use of the pre-measured blood sugar level and relative transmittances $R_{\lambda,1}$ and $R_{\lambda,2}$, and calculates the blood sugar level C in accordance with the following formula:

$$C=k_0+k_1*\ln(R_{\lambda,1})/\ln(R_{\lambda,2}),$$

in which, of the quantities of the transmitted light detected at the two positions, the quantity of the light transmitted through a shorter distance is represented as $I_{1,\lambda 1}$ and $I_{1,\lambda 2}$, the quantity of the light transmitted through a longer distance is represented as $I_{2,\lambda 1}$ and $I_{2,\lambda 2}$, and the relative transmittances $R_{\lambda,1}$ and $R_{\lambda,2}$ of the two different wavelengths are represented by the following formulae:

$$R_{\lambda,1}=I_{2,\lambda 1}/I_{1,\lambda 1} \text{ and } R_{\lambda,2}=I_{2,\lambda 2}/I_{1,\lambda 2}.$$

2. The instrument for noninvasively measuring the blood sugar level according to claim 1, wherein the lights of two different wavelengths irradiated by the irradiation device are selected within the range of 900 to 1,100 nm.

3. An instrument for noninvasively measuring a blood sugar level comprising:
- an irradiation device configured to irradiate a measurement part of a human body with the light of two different wavelengths;
- a transmitted light quantity detecting device configured to receive the transmitted light, which is the light from the irradiation device transmitted through the measurement part of the human body, at two positions spaced at different distances so as to detect the quantity of the transmitted light; and
- a calculation device configured to calculate coefficients $k_0$ and $k_1$ by the use of a pre-measured blood sugar level and absorbances $A_1$ and $A_2$, and calculates the blood sugar level C in accordance with the following formula:

$$C = k_0 k_1 * A_1/A_2,$$

in which, of the quantities of the transmitted light detected at the two positions, the quantity of the light transmitted through a shorter distance is represented as $I_{1,\lambda 1}$ and $I_{1,\lambda 2}$, the quantity of the light transmitted through a longer distance is represented as $I_{2,\lambda 1}$ and $I_{2,\lambda 2}$, the relative transmittances $R_{\lambda 1}$ and $R_{\lambda 2}$ of the two different wavelengths are represented by the following formulae:

$$R_{\lambda 1} = I_{2,\lambda 1}/I_{1,\lambda 1} \text{ and } R_{\lambda 2} = I_{2,\lambda 2}/I_{1,\lambda 2}, \text{ and}$$

the absorbances of the two different wavelengths $A_1$ and $A_2$ are represented as the following formulae on the basis of the relative transmittances $R_{\lambda 1}$ and $R_{\lambda 2}$:

$$A_1 = -\ln(R_{\lambda 1}) \text{ and } A_2 = -\ln(R_{\lambda 2}).$$

4. The instrument for noninvasively measuring the blood sugar level according to claim 3, wherein the lights of two different wavelengths irradiated by the irradiation device are selected within the range of 900 to 1,100 nm.

5. An instrument for noninvasively measuring a blood sugar level comprising:
- an irradiation device configured to irradiate a measurement pan of a human body with the light of three different wavelengths;
- a transmitted light quantity detecting device configured to receive the transmitted light, which is the light from the irradiation device transmitted through the measurement pan of the human body, at two positions spaced at different distances so as to detect the quantity of the transmitted light; and
- a calculation device configured to calculate coefficients $k_0$ and $k_1$ by the use of a pre-measured blood sugar level and relative transmittances $R_{\lambda 1}$, $R_{\lambda 2}$, and $R_{\lambda 3}$, and calculates the blood sugar level C in accordance with the following formula:

$$C = k_0 + k_1 * \ln(R_{80\ 1}/R_{\lambda 3})/\ln(R_{\lambda 2}/R_{\lambda 3}),$$

in which, of the quantities of the transmitted light detected at the two positions, the quantity of the light transmitted through a shorter distance is designated as $I_{1,\lambda 1}$, $I_{1,\lambda 2}$, and $I_{1,\lambda 3}$, the quantity of the light transmitted through a longer distance is designated as $I_{2,\lambda 1}$, $I_{2,\lambda 2}$, and $I_{2,\lambda 3}$, and the relative transmittances $R_{\lambda 1}$, $R_{\lambda 2}$, and $R_{\lambda 3}$ of the three wavelengths are represented by the following formulae:

$$R_{\lambda 1} = I_{2,\lambda 1}/I_{1,\lambda 1},\ R_{\lambda 2} = I_{2,\lambda 2}/I_{1,\lambda 2}, \text{ and } R_{\lambda 3} = I_{2,\lambda 3}/I_{1,\lambda 3}.$$

6. The instrument for noninvasively measuring the blood sugar level according to claim 5, wherein, among the lights of three different wavelengths irradiated by the irradiation device, two of the lights are selected within the range of 900 to 1,100 nm, and the other light is selected within the range of 900 to 930 nm or 1,000 to 1,030 nm.

7. An instrument for noninvasively measuring a blood sugar level comprising:
- an irradiation device configured to irradiate a measurement part of a human body with the light of three different wavelengths;
- a transmitted light quantity detecting device configured to receive the transmitted light, which is the light from the irradiation device transmitted through the measurement part of the human body, at two positions spaced at different distances so as to detect the quantity of the transmitted light; and
- a calculation device configured to calculate coefficients $k_0$ and $k_1$ by the use of a pre-measured blood sugar level and absorbances $A_1$, $A_2$, and $A_3$, and calculates the blood sugar level C in accordance with the following formula:

$$C = k_0 + k_1 * (A_1 - A_3)/(A_2 - A_3),$$

in which, of the quantities of the transmitted light detected at the two positions, the quantity of the light transmitted through a shorter distance is designated as $I_{1,\lambda 1}$, $I_{1,\lambda 2}$, $I_{1,\lambda 3}$, the quantity of the light transmitted through a longer distance is designated as $I_{2,\lambda 1}$, $I_{2,\lambda 2}$, and $I_{2,\lambda 3}$, the relative transmittances $R_{\lambda 1}$, $R_{\lambda 2}$, and $R_{\lambda 3}$ of the three different wavelengths are represented by the following formulae:

$$R_{\lambda 1} = I_{2,\lambda 1}/I_{1,\lambda 1},\ R_{\lambda 2} = I_{2,\lambda 2}/I_{1,\lambda 2}, \text{ and } R_{\lambda 3} = I_{2,\lambda 3}/I_{1,\lambda 3},$$

and the absorbances of the three different wavelengths $A_1$, $A_2$, and $A_3$ are represented by the following formulae on the basis of the relative transmittances $R_{\lambda 1}$, $R_{\lambda 2}$, and $R_{\lambda 3}$:

$$A_1 = -\ln(R_{\lambda 1}),\ A_2 = -\ln(R_{\lambda 2}), \text{ and } A_3 = -\ln(R_{\lambda 3}).$$

8. The instrument for noninvasively measuring the blood sugar level according to claim 7, wherein, among the lights of three different wavelengths irradiated by the irradiation device, two of the lights are selected within the range of 900 to 1,100 nm, and the other light is selected within the range of 900 to 930 nm or 1,000 to 1,030 nm.

* * * * *

UNITED STATES PATENT AND TRADEMARK OFFICE
CERTIFICATE OF CORRECTION

| | | |
|---|---|---|
| PATENT NO. | : 7,613,487 B2 | |
| APPLICATION NO. | : 11/734122 | |
| DATED | : November 3, 2009 | |
| INVENTOR(S) | : Yoshiaki Shimomura | |

It is certified that error appears in the above-identified patent and that said Letters Patent is hereby corrected as shown below:

Column 9:
In line 63, "$C=k_0 30\ k_1*\ln(R_{\lambda 1}/R_{\lambda 3})/\ln(R_{\lambda 2}/R_\lambda 3)\cdots (1.8)$" should be changed to
--$C=k_0+k_1*\ln(R_{\lambda 1}/R_{\lambda 3})/\ln(R_{\lambda 2}/R_{\lambda 3})\cdots (1.8)$--

Column 13, Claim 3:
In line 17, "$C=k_0 k_1*A_1/A_2$," should be changed to --$C=k_0+k_1*A_1/A_2$,--

Column 13, Claim 5:
In line 39, "pan of a human body" should read --part of a human body--

Column 13, Claim 5:
In line 44, "pan of a human body" should read --part of a human body--

Column 13, Claim 5:
In line 51, "$C=k_0+k_1*\ln(R_{801}/R_{\lambda 3})/\ln(R_{\lambda 2}/R_{\lambda 3})$," should be changed to
--$C=k_0+k_1*\ln(R_{\lambda 1}/R_{\lambda 3})/\ln(R_{\lambda 2}/R_{\lambda 3})$,--

Column 14, Claim 5:
In line 8, "$R_{\lambda 1}=I_{2,\lambda 1}/I_{1,\lambda 1}$, $R_{\lambda 2}=I_{2,\lambda 2}/I_{1,\lambda 2}$, and $R_{\lambda 3}=I_{2,\lambda 3}/I_{\lambda 3}$." should be changed
to --$R_{\lambda 1}=I_{2,\lambda 1}/I_{1,\lambda 1}$, $R_{\lambda 2}=I_{2,\lambda 2}/I_{1,\lambda 2}$, and $R_{\lambda 3}=I_{2,\lambda 3}/I_{1,\lambda 3}$.--

Column 14, Claim 7:
In line 34, "$I_{1,\lambda 2}$, $I_{1,\lambda 3}$," should be changed to --$I_{1,\lambda 2}$, and $I_{1,\lambda 3}$,--

Column 14, Claim 7:
In line 40, "$R_{\lambda 1}=I_{2,\lambda 1}/I_{1,\lambda 1}$, $R_{\lambda 2}=I_{2,\lambda 2}/I_{1,\lambda 2}$, and $R_{\lambda 3}=I_{2,\lambda 3}/I_{1,\lambda 3}$," should be changed to
--$R_{\lambda 1}=I_{2,\lambda 1}/I_{1,\lambda 1}$, $R_{\lambda 2}=I_{2,\lambda 2}/I_{1,\lambda 2}$, and $R_{\lambda 3}=I_{2,\lambda 3}/I_{1,\lambda 3}$, and--

Signed and Sealed this
Twenty-first Day of February, 2012

David J. Kappos
*Director of the United States Patent and Trademark Office*

CERTIFICATE OF CORRECTION (continued)
U.S. Pat. No. 7,613,487 B2

Column 14, Claim 7:
In line 40, delete the word "and"